US009492509B2

(12) United States Patent
Gasull Dalmau et al.

(10) Patent No.: US 9,492,509 B2
(45) Date of Patent: Nov. 15, 2016

(54) APOTRANSFERRIN FOR THE TREATMENT OF BRAIN STROKE

(71) Applicants: FUNDACIÓ INSTITUT D'INVESTIGACIÓ EN CIÈNCIES DE LA SALUT GERMANS TRIAS I PUJOL, Badalona (ES); INSTITUTO DE INVESTIGACIÓN SANITARIA—FUNDACIÓN PARA LA INVESTIGACIÓN DEL HOSPITAL LA FE, Valencia (ES); UNIVERSITAT AUTÓNOMA DE BARCELONA, Bellaterra (Cerdanyola) (ES)

(72) Inventors: Teresa Gasull Dalmau, Sabadell (ES); Núria Degregorio-Rocasolano Barbany, Santa Coloma de Gramenet (ES); Antonio Dávalos Errando, Girona (ES); Juan B. Salom Sanvalero, Carcaixent (ES); Enrique Alborch Domínguez, Valencia (ES); Octavi Martí Sistac, Sabadell (ES)

(73) Assignees: FUNDACIÖ INSTITUT D'INVESTIGACIÓ EN CIÈNCIES DE LA SALUT GERMANS TRIAS I PUJOL, Badalona (ES); INSTITUTO DE INVESTIGACIÓN SANITARIA—FUNDACIÓN PARA LA INVESTIGACIÓN DEL HOSPITAL LA FE, Valencia (ES); UNIVERSITAT AUTÒNOMA DE BARCELONA, Bellaterra (ES)

( * ) Notice: Subject to any disclaimer, the term of this patent is extended or adjusted under 35 U.S.C. 154(b) by 0 days.

(21) Appl. No.: 14/357,518

(22) PCT Filed: Nov. 8, 2012

(86) PCT No.: PCT/EP2012/072195
§ 371 (c)(1),
(2) Date: May 9, 2014

(87) PCT Pub. No.: WO2013/068504
PCT Pub. Date: May 16, 2013

(65) Prior Publication Data
US 2014/0323409 A1    Oct. 30, 2014

(30) Foreign Application Priority Data

Nov. 11, 2011    (ES) .................................. 201131816

(51) Int. Cl.
*A61K 38/00* (2006.01)
*A61K 38/40* (2006.01)
*A61K 31/16* (2006.01)
*A61K 45/06* (2006.01)

(52) U.S. Cl.
CPC ............... *A61K 38/40* (2013.01); *A61K 31/16* (2013.01); *A61K 45/06* (2013.01)

(58) Field of Classification Search
None
See application file for complete search history.

(56) References Cited

FOREIGN PATENT DOCUMENTS

| WO | WO0001407 A1 | 1/2000 |
| WO | WO2006020727 A2 | 2/2006 |

OTHER PUBLICATIONS

Clausi et al., ASN Neuro, 2010, 2(5):239-309.*
Smith et al., Am. J. Physiology—Heart and Circulatory Physiology, 1989, 256(5):25/5.*
"Tissue plasminogen activator for acute ischemic stroke", N. England J. Med., 1995, 333(24):1581-8.*
Palmer et al., Stroke, 1994, 25:1039-45.*
Andrews, Nancy C. et al., "Iron Homeostasis: Insights From Genetics and Animal Models". Nature Reviews Genetics, Dec. 2000, vol. 1, pp. 208-217, Macmillan Magazines Ltd, London England.
Benarroch, Eduardo E, "Brain Iron Homeostasis and Neurodegenerative Diseases", Neurology, Jun. 2010, vol. 72, pp. 1436-1440, AAN Enterprises, Inc., Minneapolis, MN.
Chen-Roetling, Jing et al: "Apotransferrin protects cortical neurons from haemoglobin toxicity", Neuropharmacology, Feb. 2011, vol. 60, No. 2-3, pp. 423-431, Pergamon Press, Oxford, GB. [XP027579467, ISSN: 0028-3908 (abstract retrieved on Oct. 27, 2010 * p. 430, 1 ast *; p. 5F; figures 1-7.)].
Chen-Roetling, Jing et al "Iron accumulation and neurotoxicity in cortical cultures treated with holotransferrin," Free Radical Biology & Medicine, Dec. 2011, vol. 51, No. 11, pp. 1966-1974, Elsevier, Inc. Philadelphia, PA. (Epub: Aug. 30, 2011).
De Vries, Bart et al., "Reduction of circulating redox-active iron by apotransferrin protects against renal ischemia-reperfusion injury.", Transplantation, Mar. 15, 2004, vol. 77, No. 5, pp. 669-675, Lippincott Williams & Wilkins, Philadelphia, PA. (XP002689444, I SSN: 0041-1337 abstract; figures 1-7).
Green A R: "Pharmacological approaches to acute ischaemic stroke: reperfusion certainly, neuroprotection possibly.", British Journal of Pharmacology, Mar. 2008, vol. 153 pp. S5325-S5338, Nature Publishing Group, New York, NY. (XP002689443. ISSN: 0007-1188 * p. 5329-5330: Metal chelation. PAN-8U *).
Heikkinen, Janne et al., "Apotransferrin, C1-esterase inhibitor, and alpha 1-acid glycoprotein for cerebral protection during experimental hypothermic circulatory arrest.", Scandinavian Cardiovascular Journal, Jun. 2004, vol. 38, No. 3, pp. 178-186, Taylor & Francis Health Sciences, United Kingdom. (XP9165752, ISSN: 1401-7431 abstract * p. 179, col. 1 Materials and methods, 1 *).

(Continued)

*Primary Examiner* — Olga N Chernyshev
(74) *Attorney, Agent, or Firm* — Peter B. Scull; Hamilton, DeSanctis & Cha, LLP

(57) ABSTRACT

The present invention relates to the use of apotransferrin for the preparation of a medicament for the treatment of brain stroke. Particularly the invention relates to the use of apotransferrin for the preparation of a medicament for the treatment of brain strokes wherein the drug prepared with apotransferrin is for administration by vascular route, preferably intravenous or intraarterial.

10 Claims, 5 Drawing Sheets

(56) References Cited

OTHER PUBLICATIONS

Hernandez, Lucrecia Anzueto et al., "A role for iron in oxidant-mediated ischemic injury to intestinal microvasculature.", Iron and Ischemic Injury, Jul. 1987, vol. 253, No. 1, Jul. 1987, pp. G49-G53, American Physiological Society, Rockville MD. (XP9165757, ISSN: 0002-9513 abstract; figure 1).

Longa, E.Z., et al. "Reversible middle cerebral artery occlusion without craniectomy in rats". Stroke, Jan. 1989, vol. 20, No. 1, p. 84-91, American Hearth Association, Dallas, TX.

Lorberboym Mordechai, et al."In vivo imaging of apoptosis in patients with acute stroke: Correlation with blood-brain barrier permeability", Brain Research, Aug. 2006, vol. 1103, No. 1, pp. 13-19, Elsevier, Amsterdam, NL. (XP027918058, ISSN: 0006-8993 [retrieved on Aug. 4, 2006] abstract * p. 14, 2.4 OTPA Spect imaging *).

Munshi A, et al., "Depletion of serum zinc in ischemic stroke patients". Methods and Findings in Experimental and Clinical Pharmacology, Jul.-Aug. 2010, vol. 32(6), pp. 433-436, Thomson Reuters, New York, NY.

Ponce, Jovita et al. "The effect of simvastatin on the proteome of detergent resistant membrane domains: decreases of specific proteins previously related to cytoskeleton regulation, calcium homeostasis and cell fate", Proteomics Journal, Feb. 2010, vol. 10, p. 1954-1965, Wiley-VCH Verlag GmbH & Co, Weinheim, Germany.

Rudolph, Joseph G et al. "Use of a multiwell fluorescence scanner with propidium iodide to assess NMDA mediated excitotoxicity in rat cortical neuronal cultures". Neuroscience Letters, Jan. 1997, vol. 221, No. 2-3, p. 149-152, Elsevier Science Ireland Ltd, Ireland.

Palaniswami, Murugan, et al., Mechanical Thrombectomy is Now the Gold Standard for Acute Ischemic Stroke: Implications for Routine Clinical Practice, Interventional Neurology, Sep. 18, 2015, pp. 12, vol. 4:18-19, S. Karger AG, Basel, Switzerland.

* cited by examiner

A

B

A

B

APOTRANSFERRIN FOR THE TREATMENT OF BRAIN STROKE

The present invention is related to the field of medicine, and particularly to the field of cerebrovascular accidents. It specifically relates to the use of apotransferrin for the treatment of brain stroke.

BACKGROUND ART

Cerebral ischemia is the reduction in blood flow to levels that are insufficient to maintain the metabolism necessary for normal function and structure of the brain. When the blood supply decreases, the supply of oxygen, nutrients and the elimination of products from the metabolism of a biological tissue also decreases, all of which produces damages in the brain tissue.

Cerebral ischemia may be total or partial, depending on whether it affects all the brain or just one or several areas. Frequent causes of total cerebral ischemia are the decrease in cardiac output (cardiac arrest or arrhythmias) and the decrease in peripheral resistance (systemic shock, cardiovascular surgery or hypotension during anaesthesia due to general surgery). The most frequent cause of partial cerebral ischemia is a brain stroke.

A brain stroke is a cerebral circulation disorder which causes a transient or definitive alteration of the functioning of one or several parts of the brain. According to its aetiology, the brain stroke may be ischemic or haemorrhagic. An ischemic stroke arises when the brain loses blood supply due to the sudden and immediate interruption of blood flow, which frequently occurs due to the occlusion of any of the arteries that supply the brain matter because of a blood clot. In contrast, the haemorrhagic stroke is triggered by the rupture of an encephalic blood vessel due to a hypertensive peak, a congenital aneurism, or other less frequent causes.

The affectation of specific areas of the brain by brain strokes generates focalized manifestations such as paralysis or plegia of a hemibody (one half of the body), facial paralysis, aphasia (loss of the capacity to produce or understand language) and disorientation, among others. In general, the symptoms of strokes are variables depending on the brain area affected. In milder cases, the consequences may go unnoticed and may not be greatly limiting for the patient due to the anodyne nature of the symptoms. However, strokes frequently cause permanent neuronal damage or result in the death of the individual. Indeed, brain stroke is one of the main causes of mortality and of permanent incapacity in adults in the majority of developed countries.

As previously commented, the damages caused by cerebral ischemia after a stroke are related to the malfunctioning of brain tissue and its possible death due to lack of energy. To re-establish the energy supply after an ischemic episode it is, therefore, necessary to re-establish the blood supply in the affected area.

To date, the only pharmacological treatment approved for the treatment of strokes is tissue plasminogen activator (tPA) by intravenous route. tPA has a thrombolytic effect, i.e. it produces the disintegration of the clot which causes the lack of blood supply in the brain area at risk. Therefore, this treatment is only indicated for ischemic stroke patients, its use being counterproductive in haemorrhagic stroke patients. Another way of re-establishing blood flow is by a surgical intervention that eliminates the occlusion.

Whatever the treatment, it is important that it is promptly carried out in order to avoid major damages in the tissue caused by cerebral ischemia. The administration of tPA is only indicated if it is performed during the first 4.5 hours after the start of symptoms, although it could also be effective some hours later in those cases where there is still recoverable tissue. This means that the therapeutic window of the thrombolytic treatment available is very small. Furthermore, although the re-establishing of the blood flow (process known as reperfusion) puts an end to the situation of ischemia, it entails new damages in the brain tissue (damages due to reperfusion).

The damages due to reperfusion are due to the inflammatory response of the tissues affected by ischemia and, very particularly, to the induction of oxidative stress caused by the sudden availability of oxygen. These damages significantly contribute to the detriment in the stroke patient's health. Despite the fact that great efforts are being made that permit minimizing the damages caused by ischemia and reperfusion, to date there are no effective strategies for this.

An area of research to limit the negative effects of reperfusion is therapeutic hypothermia. Hypothermia can help to moderate the intracranial pressure and, therefore, reduce the harmful effects of the patient's inflammatory immune response and the production of free radicals during reperfusion. However, this therapy is complex in its application and its effects are limited.

Some studies suggest the use of iron chelating agents to avoid damages due to reperfusion. During reperfusion, the iron transported by the blood is capable of catalysing reactions that produce reactive oxygen species, mainly hydroxyl radicals. These radicals, in turn, start the peroxidation of the lipids, cause the degradation of the DNA and inactivate enzymes. Due to its high lipid content, the brain is especially sensitive to peroxidation, which causes considerable damages during reperfusion. International patent application WO2006/20727 proposes the use of deferoxamine as neuroprotector agent against the harmful effects of reperfusion. However, the administration of deferoxamine poses problems due to its reduced half-life in plasma and because its intravenous injection may cause hypotension with the risk of lethal shock, so that it is only effective when administered by intranasal route in the upper part of the nasal cavity.

Thus, it would be desirable to find new strategies for treating brain strokes.

SUMMARY OF THE INVENTION

Surprisingly, the present inventors have found that the administration of apotransferrin (or iron-free transferrin) to the bloodstream of a patient considerably reduces the damages caused after a brain stroke.

Thus, in a first aspect, the invention provides the use of apotransferrin for the preparation of a medicament for the treatment of brain stroke. This aspect can be reformulated as apotransferrin for the treatment of brain stroke.

The invention also relates to a method of treatment of brain stroke by the administration of apotransferrin to an animal in need thereof. In a particular embodiment, the animal is a mammal, preferably a human.

"Brain stroke" (also called cerebral infarction, cerebrovascular accident, apoplexia or simply stroke) is understood to be a cerebral circulation disorder that causes a transient or definitive alteration in the functioning of one or several parts of the brain. When it only affects one area of the brain, the stroke is called "focal brain stroke". In some cases the brain stroke is transient, with the blood flow returning to the affected area after a certain time (a process called "reperfusion"). On other occasions, a significant reperfusion of the tissue does not occur, giving rise to a permanent brain stroke. On the other hand, depending on its aetiology, the stroke may be ischemic ("ischemic stroke") or haemorrhagic ("haemorrhagic stroke") depending on whether it is produced as a consequence of the occlusion of any of the arteries that supply the brain matter or the rupture of an encephalic blood vessel, respectively.

"Apotransferrin" is the fraction of transferrin that is free from iron. Transferrin, or siderophilin, is the protein that transports iron in the blood. It is a beta-2 globulin, with ellipsoid form and with a molecular weight that varies between 70,000 and 95,000 daltons which has two active iron binding sites. When the transferrin is iron-free it is called apotransferrin. When the transferrin is saturated with iron it is called holotransferrin. The use of apotransferrin in the treatment of brain strokes has the advantage that it is an endogenous protein in animals, which entails a lower risk of generating adverse reactions in the organism. Preferably, the apotransferrin for its use in the present invention is human apotransferrin.

In an embodiment of the first aspect of the invention the apotransferrin is administered by vascular route.

"Administration by vascular route" is understood as any route of administration where the drug is introduced in the bloodstream, whereby it reaches the damaged tissue. Non-limiting examples of routes of administration that introduce the drug in the bloodstream are: the intravenous (IV) and intraarterial (IA) routes, which introduce the drug directly in the bloodstream, as well as sublingual, conjunctive, subcutaneous, intramuscular, intradermal, rectal, oral and topical routes, which introduce the drug indirectly in the bloodstream.

Thus, in a particular embodiment, the invention provides the use of apotransferrin in the preparation of a medicament for the treatment of brain stroke, where the medicament prepared with apotransferrin is administered by vascular route. This embodiment can be reformulated as apotransferrin for the treatment of brain stroke, where the apotransferrin is administered by vascular route.

The invention also relates to a method of treatment of brain stroke by the administration by vascular route of apotransferrin to a patient in need thereof.

The fact that the administration of apotransferrin to the bloodstream is effective for the treatment of brain stroke is surprising, since it is known that apotransferrin is not capable of crossing the hematoencephalic barrier (Andrews N, et al. "Iron homeostasis: insights from genetics and animal models". *Nature Reviews Genetics,* 2000, vol. 1, p. 208-217). However, the inventors have demonstrated the efficacy of apotransferrin administered to the bloodstream by intravenous route (IV) in the treatment of damages due to ischemia-reperfusion in two in vivo experimental models of transient ischemic focal stroke (see FIG. 1 and FIG. 2). Both models studied the affectation of the brain tissue of rats subjected to ischemia-reperfusion 24 h after the administration of apotransferrin by IV injection in comparison with controls that were not administered apotransferrin. The results clearly indicate that the volume of damaged tissue is significantly less in the animals treated with apotransferrin.

The inventors have observed that, surprisingly, the vascular administration (by IV route) of apotransferrin is also beneficial in the absence of reperfusion or restoration of the blood flow. FIG. 3 shows the results obtained with the administration of apotransferrin in an in vivo experimental model of permanent focal ischemic stroke. In this model the apotransferrin was administered by IV route 50 min after a permanent occlusion of the middle cerebral artery in the rats had taken place, without reperfusion. It is observed that the rats treated with apotransferrin by IV route show less brain damage than the untreated controls; particularly, it is observed that the volume of the damaged brain area in the rats treated with apotransferrin is 50% smaller. Furthermore, the preliminary results of neurological tests indicate that the rats subjected to a permanent occlusion of the middle cerebral artery show less neurological deficit and perform motor tasks involving the ischemic brain area with greater efficiency when treated with apotransferrin.

The use of apotransferrin in the treatment of brain strokes has, therefore, the additional advantage that its efficacy goes beyond reducing damages due to reperfusion, producing beneficial effects in those brain stroke patients that cannot be treated with thrombolytic agents, with neurointervention or in any other way. The clinical relevance is significant since, to date, patients in that situation cannot benefit from any treatment.

On the other hand, the efficacy of apotransferrin in reducing the damages caused by cerebral ischemia after a stroke contrasts with the harmful effects of holotransferrin. FIG. 4 demonstrates that IV administration of holotransferrin induces neuronal death and an extensive production of free radicals in cultured neurons subjected to an in vitro model of ischemia called oxygen-glucose deprivation (OGD). Thus, of the existing fractions of transferrin, only apotransferrin is capable of exercising beneficial effects in ischemic tissue. Furthermore, holo-transferrin administered intravascularly before the ischemia occurs increases the infarction volume assessed in the first hours after the start of the occlusion in an in vivo experimental stroke model (FIG. 5).

The vascular administration routes include IV and IA injection. These administration routes involve various advantages regarding speed of action (the drug quickly reaches the affected area), ease of administration, control of the dose, etc. Thus, treatment with apotransferrin for brains stroke can be directly administered to the bloodstream through an intravenous or intraarterial catheter, which is very convenient in patients that, as in the case of brain stroke patients, are either too agitated, or unable to perform simple actions such as ingesting a drug. On the other hand, the administration of apotransferrin by IV or IA route facilitates the administration of this active agent together with a thrombolytic agent, such as tPA, or another therapeutic agent, in a combined therapy for the treatment of brain stroke.

The invention also contemplates the administration of apotransferrin by another route of vascular administration, for example, oral or sublingual. Additionally, the invention contemplates the administration of apotransferrin by epidural injection, intracranial injection or intranasal application.

Thus, in a particular embodiment the route of administration of apotransferrin is intravenous or intraarterial. In another particular embodiment the route of administration of apotransferrin is sublingual. In another particular embodiment the route of administration is intranasal.

The administration of apotransferrin according to the invention is useful for the treatment of brain stroke irrespective of the cause and extent of the stroke. Thus, the invention relates to the treatment of permanent or transient brain strokes, as well as to the treatment of a brain stroke caused by a clot (ischemic) or by a haemorrhage (haemorrhagic).

In a particular embodiment, the invention provides apotransferrin for the treatment of a haemorrhagic brain stroke.

In another particular embodiment, the invention provides apotransferrin for the treatment of an ischemic brain stroke. In another particular embodiment, the stroke is an acute focal ischemic stroke.

In one embodiment, the invention provides apotransferrin for the treatment of a permanent brain stroke. In another embodiment apotransferrin is provided for the treatment of a transient brain stroke.

Patients who have suffered an ischemic stroke may on occasions be susceptible to treatment with thrombolytic therapy. In these cases, the treatment of the stroke with thrombolytic therapy can be advantageously combined with apotransferrin-based therapy. Whilst the thrombolytic agent makes it possible to re-establish blood circulation in the affected area, apotransferrin minimizes the damages produced by the ischemia and the reperfusion, avoiding major damages to the tissue. Thus, in a particular embodiment, the invention provides apotransferrin for the treatment of ischemic brain stroke in combination with a thrombolytic agent. Preferably, the thrombolytic agent is a human tissue plasminogen activator.

In general, treatment with apotransferrin will be performed as soon as possible in order to avoid major damages to the brain tissue, so that the medical professional may consider it suitable to administer apotransferrin as soon as the stroke patient comes into his care. In some cases, such as patients susceptible to being treated with thrombolytic therapy, the apotransferrin can be administered at the time of reperfusion. "At the time of reperfusion" is understood to range from two hours before to 2 hours after reperfusion, as well as right at the same time of reperfusion. This implies that the apotransferrin can be administered at the same time as a thrombolytic agent is administered, or at the time of performing a surgical intervention to eliminate the clot obstructing the blood flow. In the cases wherein the restoration of the blood flow is non-existent or very limited, the administration of apotransferrin is also beneficial and, in general, this will be performed as soon as possible after the diagnosis.

The present invention also provides the use of apotransferrin for the treatment of brain stroke patients in combination with other therapies. Suitable therapies for their use in combination with apotransferrin-based therapy are, as previously mentioned, thrombolytic treatment and/or surgical intervention to eliminate the cause of ischemic stroke. Other suitable therapies for their use in combination with apotransferrin-based therapy are, without limitation, surgical intervention to slow the haemorrhage that caused the haemorrhagic stroke, treatment with citicoline, with chelating agents, with antioxidant agents, with excitotoxic damage limiters, with anti-inflammatory agents, with fluoxetine, or together with other apoforms of iron transporting molecules that use receptors for their transport such as, for example, lactoferrin.

In a particular embodiment, the apotransferrin is used in combination therapy with a chelating agent, for example an iron-chelating agent. In another particular embodiment, the chelating agent is deferoxamine. In another particular embodiment, the apotransferrin is used in combination therapy with a chelating agent of another metal different to iron. In another particular embodiment the apotransferrin is used in combination with citicoline. Citicoline (cytidine 5'-diphosphocholine) is an intermediate in the synthesis of phosphatidylcholine from choline which has demonstrated a beneficial effect in the evolution of hypoxia and cerebral ischemia.

The person skilled in the art understands that combination therapy is effective when the therapeutic agents are administered forming part of the same composition, but also when they form part of different compositions, whether for simultaneous, sequential or separate administration. On the other hand, the person skilled in the art will understand that apotransferrin can be prescribed for the treatment of brain stroke with an indication for use in combination with another active agent.

The invention also refers to pharmaceutical compositions that comprise a therapeutically effective quantity of apotransferrin, together with sufficient quantities of pharmaceutically acceptable excipients and carriers. In a particular embodiment, the pharmaceutical composition of the invention is designed for its vascular administration, for example for its administration by IV or IA route.

For "pharmaceutically acceptable" is understood that compounds, materials or compositions are appropriate to be administered in an animal, including a human, without inducing toxicity, irritation, incompatibility, instability, allergic response or the like. Each pharmaceutically acceptable excipient or carrier must also be acceptable in the sense of being compatible with the other ingredients of the pharmaceutical composition of the invention. The compositions of the present invention may additionally comprise components that allow a controlled release or greater comfort.

Preferably, the compositions of the invention shall be administered to patients by IV or IA route. As the persons skilled in the art can appreciate, the compositions may be prepared in different forms suitable for administration by IV or IA route. In a particular embodiment, the composition comprises apotransferrin and physiological serum.

In the therapeutic applications, the active agents are administered to a patient that suffers from a disease in a therapeutically effective quantity. "Therapeutically effective quantity" is understood to be a quantity of active agents sufficient to provide benefits to the patient. The quantity of apotransferrin that the pharmaceutical composition of the invention comprises may be determined by a person skilled in the art following standard protocols in the field of clinical medicine. The therapeutically effective quantity is also known as the dose. The exact dose will depend on the administration route, the severity of the disease and the general state of health of the patient. The patient can be administered single or multiple doses (at time intervals) of the active agent. For example, for IV or IA administration of apotransferrin it is possible to use quantities between 1 and 2,000 mg per kg of weight, or between 10 and 1,500 mg per kg of weight or between 50 and 1,000 mg per kg of weight, or between 100 and 800 mg per kg of weight, or between 100 and 600 mg per kg of weight, or between 120 and 500 mg per kg of weight, or between 150 and 400 mg per kg of weight.

Apotransferrin for its use in the present invention can be prepared by methods known in the state of the art. For example, international patent application WO2000/001407 discloses methods to prepare human apotransferrin for pharmaceutical compositions. It is also possible to obtain apotransferrin in recombinant form.

The present invention also contemplates a pharmaceutical composition which comprises a therapeutically effective quantity of apotransferrin, together with sufficient quantities of pharmaceutically acceptable excipients and carriers, for their use in the treatment of brain stroke. This can be reformulated as the use of a pharmaceutical composition that comprises a therapeutically effective quantity of apotransferrin, together with sufficient quantities of pharmaceutically acceptable excipients and carriers, for the preparation of a medicament for the treatment of brain stroke. In a particular embodiment, the treatment of brain stroke is carried out by administering the composition of the invention by vascular route, for example by IV or IA route, and the composition is formulated for its administration by IV or IA route.

Finally, the invention also relates to a method of treatment of brain stroke comprising administering to the patient, preferably by vascular route, a pharmaceutical composition comprising a therapeutically effective quantity of apotransferrin, together with sufficient quantities of pharmaceutically acceptable excipients and carriers.

Throughout the description and the claims the word "comprises" and its variants are not intended to exclude other technical characteristics, additives, components or steps. For persons skilled in the art, other objects, advantages and characteristics of the invention will be inferred in part from the description and in part from the practice of the invention. Furthermore, the present invention covers all the possible combinations of particular and preferred embodiments indicated herein.

BRIEF DESCRIPTION OF THE DRAWINGS

FIG. 1 is related to section 1 of the results.

FIG. 2 is related to section 1 of the results.

FIG. 3 is related to section 1 of results.

FIG. 4 is related to section 2 of the results.

FIG. 5 is related to section 2 of the results.

EXAMPLES

Figure 1:
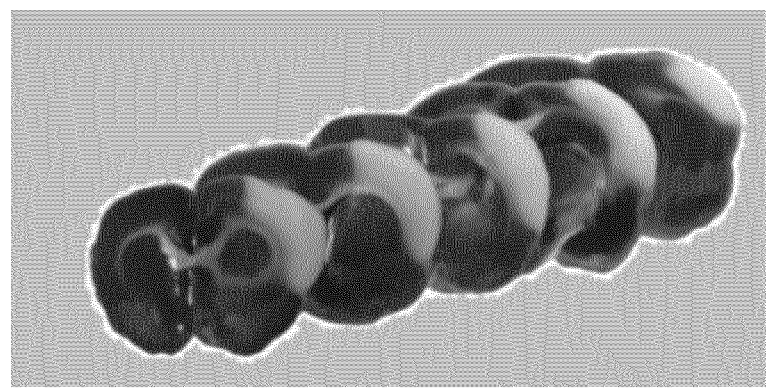
FIG. 1. Volume of cortical infarction induced in rats by 60 min of occlusion of the middle cerebral artery by ligation. A, image of the affected area in the rats' brains. B, percentage of the volume of infarcted brain tissue with administration of: (2) apotransferrin or (1) carrier. With respect to the examples.
Figure 1:
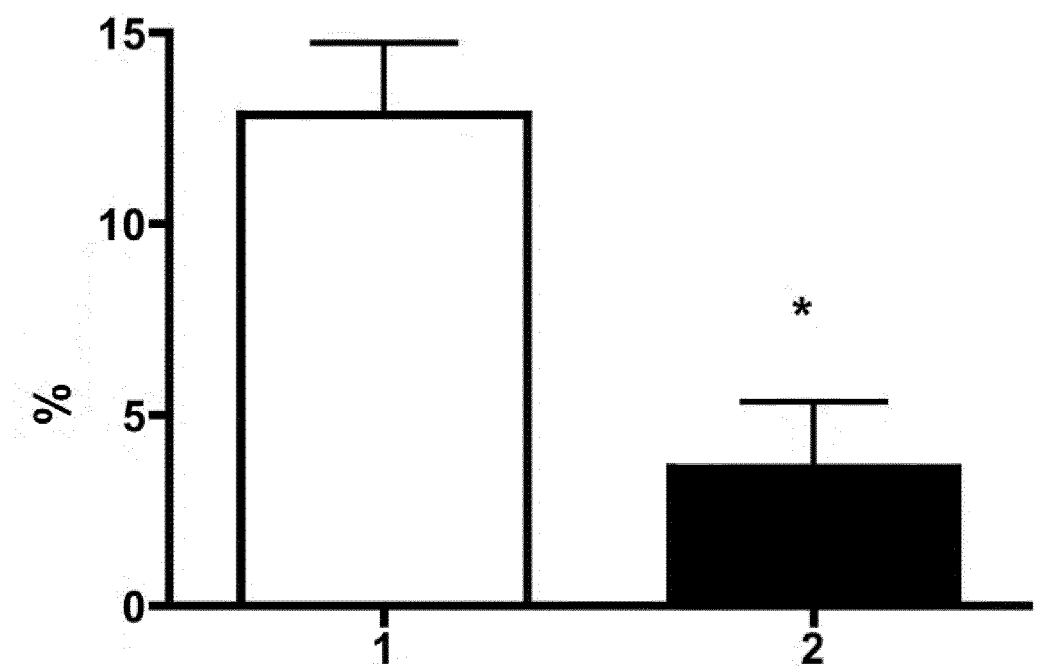

The following examples are provided by way of illustration and without intending to be limiting for the present invention.

Materials and Methods

1. In Vitro Model 1.1. Primary culture of rat brain cortex neurons. The cortical neuron cultures were prepared following the previously described protocol (Ponce J., et al. "The effect of simvastatin on the proteome of detergent resistant membrane domains: decreases of specific proteins previously related to cytoskeleton regulation, calcium homeostasis and cell fate", *Proteomics* 2010, vol. 10, p. 1954-1965), although the neurons were seeded in 24-well plates.

1.2. Oxygen-glucose deprivation. The studies were performed on 11 days-cultured neurons. To produce the oxygen-glucose deprivation (OGD) the conditioned culture medium was removed and kept separately. The cells exposed to OGD were incubated during 90 min with Dulbecco's modified Eagle medium (DMEM) (Invitrogen, Barcelona, Spain) in an atmosphere containing 0.1% $O_2$. The control cells were incubated with DMEM supplemented with 4.5 g/l of glucose in normoxic conditions. The reperfusion was produced by returning the conditioned medium and normoxia conditions to the cells during 30 min.

1.3. Treatments in neuron cultures. The cultured cortical neurons were treated with $FeCl_3$ (10-50 µM), holo-transferrin (HTf) (1-5 µM) or apotransferrin (1-5 µM) (Sigma, Madrid, Spain) during the reperfusion period.

1.4. Determination of cell death. The cell death studies were determined following the measurement of the incorporation of propidium iodide into the cells (Sigma, Madrid, Spain) using the previously described method (Rudolph J. G., et al. "Use of a multiwell fluorescence scanner with propidium iodide to assess NMDA mediated excitotoxicity in rat cortical neuronal cultures". *Neurosci. Lett.,* 1997, vol. 221, p. 149-152).

1.5. Production of oxygen free radicals. As an index for .OH+peroxide production the conversion of the compound 5-(and -6)-chloromethyl-2,7-dichlorodihydrofluorescein diacetate mixed isomers, acetyl ester (CM-H2DCFDA) (Invitrogen, Barcelona, Spain) to dichlorofluorescein (DCF). Neurons exposed to OGD were reperfused during 30 min in the presence or absence of 5 µM HTf or 50 µM $FeCl_3$. The compound CM-H2DCFDA (10 µM) was added to the reperfusion medium and microscope images were acquired with the suitable filter as indicated by the manufacturer. The signal intensity was quantified using the Image J program (NIH, USA).

2. In Vivo Models

All experimental protocols in which animals took part were approved by the animal experimentation ethics committee of the Fundació Institut D'investigació en Ciències de la Salut Germans Trias i Pujol. The animals were anaesthetized by exposure to 5% isofluorane or 2% sevoflurane in a mixture of 30/70% $O_2/N_2O$. The animals remained anaesthetized throughout the surgical procedure due to inhalation of a maintenance dose of anaesthesia of 1.5-2.0% isofluorane or 0.5-1 sevoflurane in a mixture of 30/70% $O_2/N_2O$. Once the interventions to perform the experimental stroke models were finished, the surgical incisions were sutured and the animals were returned to their cages, remaining in them for 24 h until the time of performing the post-ischemia neurological tests and the sacrifice of the animal. In some cases, the animals underwent neurological tests in the days prior to performance of the surgery and these results were compared with the results of the identical tests performed post-surgery.

2.1. Process of Transient Focal Cerebral Ischemia Performed by Ligation of the Middle Cerebral Artery (MCA).

Male Sprague-Dawley rats (250-270 g, Harlan Laboratories, Barcelona) were subjected to a small craniectomy to expose the middle cerebral artery which was ligated just before its bifurcation in the frontal and parietal branch just before the ophthalmic branch. The interruption of the blood flow was verified under surgical magnifying glass and both carotid arteries were occluded during 60 min. At the end of the 60 min both carotids and the middle cerebral artery were deligated, and immediately after carrier solution (physiological saline solution) or 50 mg of apotransferrin (Sigma, Madrid, Spain) in carrier solution was administered directly to the intravascular compartment by injection in the animal's tail vessels.

2.2. Process of Permanent Focal Cerebral Ischemia Performed by Ligation of the MCA.

The protocol is identical to that described in section 2.1. except that the MCA and the left carotid remain ligated until the time of sacrifice of the animal and that the carrier or the apotransferrin were administered 50 min after the start of the ischemia.

2.3. Process of Transient Focal Cerebral Ischemia Using Intraluminal Filament Effect of the Administration of Apotransferrin.

Male Wistar rats (300-350 g, Charles River Laboratories, Barcelona, Spain) were anaesthetized with an injection of 5 mg/kg diazepam (Almirall Prodesfarma, Barcelona, Spain), 100 mg/kg ketamine (Ketolar, Parke-Davis, El Prat de Llobregat, Barcelona, Spain) and 0.3 mg/kg atropine (B Braun Medical, Rubí, Barcelona, Spain) to allow their intubation for mechanical ventilation (Harvard Apparatus, 683 rodent ventilator, Holliston, Mass., USA). The anaesthesia was prolonged by exposure to 0.5-1% sevoflurane (Sevorane, Abbott Laboratories, Madrid, Spain) in a mixture of 30/70% $O_2/N_2O$. Focal ischemia was induced in the right hemisphere using a nylon filament which is introduced until occluding the MCAO following the protocol described by Longa E. Z. et al. (Longa E. Z., et al. "Reversible middle cerebral artery occlusion without craniectomy in rats". *Stroke* 1989, vol. 20, p. 84-91). The occlusion and reduction of blood flow were measured with a laser-doppler probe fixed to the skull in the parietal area adjacent to the end of the supply area of the MCA. 90 min after the start of the ischemia, the intraluminal filament was removed, there was a wait of 5-10 min to verify the effective re-establishment of the blood flow to its previous levels, and a total of 100 mg of apotransferrin was intravascularly administered in two administrations performed with 30 min difference (Sigma, Madrid, Spain). As control, rats were used which carrier had been administered instead of apotransferrin.

2.4. Transient Focal Cerebral Ischemia Using Intraluminal Filament. Effect of the Administration of Holotransferrin.

In this experiment, the same process described by Longa E. Z. et al. was used but in male Sprague-Dawley rats of 250-280 g (Animal house of the University of Santiago de Compostela, Santiago de Compostela, Spain). Furthermore, the animals were intravascularly injected with 85 mg of holotransferrin or carrier 10 min before starting the occlusion. After performing the occlusion, the animals were introduced in a nuclear magnetic resonance apparatus (9.4 T) (Bruker Biospan, Ettlingen, Germany) to determine the volume of hypoperfused brain tissue during the 90 min of ischemia and the diffusion-weighted imaging (DWI) sequence corresponding to a damaged brain area. Various determinations were performed at 15 min intervals throughout the 90 min of ischemia and until reaching 165 min from the start of the occlusion.

2.5. Neurological Tests

The performed unilateral focal cerebral ischemia only affects the sensorial and motor function of the contralateral side of the animal. A battery of neurological tests was performed in order to evaluate the degree of left and right sensorial and motor cerebral affectation of the animal. The result of all these tests was a neurological deficit value that correlated with the infarction volume. A baseline pre-test was performed for each animal as a control before performing the focal ischemia. The following tests were carried out, which are well known in the state of the art:

2.5.1. Whiskers test: The response of each animal to the stimulation of the whiskers on the left and right side, performed so that the animal has no visual information in this regard, was assessed.

2.5.2. Prehensile capacity test: The time was measured in which the animal was capable of holding on bearing its own weight by its two upper limbs to a suspended rod.

2.5.3. Corner turn test: The animals' ability was assessed to turning to the right or left when placed in front of a 30° angle so that it must turn to move.

2.5.4. Sticker test: A sticker was attached to each of the animal's upper limbs and it was measured how long the animal took to pull each sticker off.

2.5.6. Tail suspension test: The percentage and the angle of body rotations to the right and left that the animal performed suspended by its tail was recorded.

2.5.7. Grille test: this evaluates the force that the animal can exert with its upper limbs gripping on a grille.

2.6. Determination of the infarction volume.

Once the animal was sacrificed 24 hours after the start of the cerebral ischemia, the brain was dissected and it was cut in 2 mm coronal slices which were incubated with a 1% 2,3,5-triphenyltetretazolium chloride (TTC) solution (Sigma, Madrid, Spain) during 20 min at 37° C. The slices were photographed and the percentage of brain area not stained with TTC with respect to the area present in the ipsilesional hemisphere was calculated. The area not stained with TTC corresponds to the area damaged by the stroke.

Results

1. The Intravenous Administration of Apotransferrin Considerably Reduces the Neuronal Damages Caused After a Brain Stroke.

Figure 2:
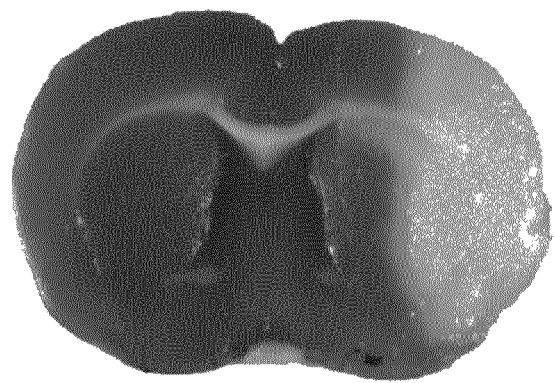
FIG. 2. Volume of cortical infarction induced in rats by 90 min of occlusion of the middle cerebral artery by intraluminal filament. A, image of the affected area in the rats' brains. B, percentage of the volume of infarcted tissue with administration of: (2) apotransferrin or (1) carrier. With respect to the examples.
Figure 2:
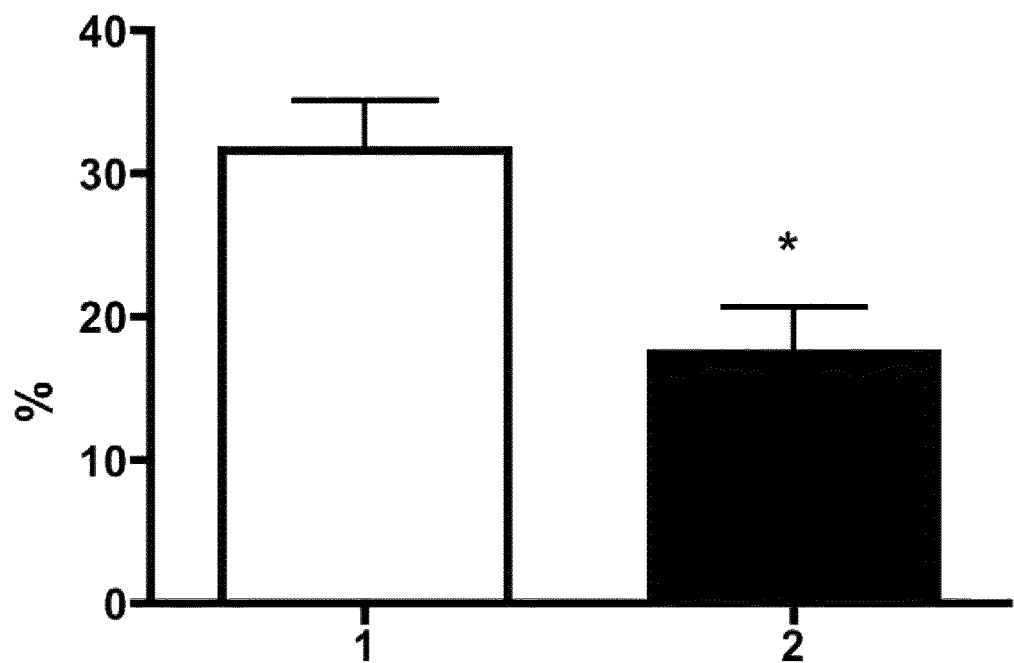

FIGS. 1 and 2 show the efficacy of the apotransferrin administered to the bloodstream by intravenous route in the treatment of cerebral ischemia in two in vivo experimental models of transient focal ischemic stroke. FIG. 1 represents the reduction in the volume of cortical infarction induced by 60 min of occlusion of the middle cerebral artery by ligation of the MCAO in the animals treated with apotransferrin in comparison with the controls that were only administered carrier. FIG. 2 represents the reduction in the infarction volume induced by 90 min of occlusion of the middle cerebral artery by intraluminal filament in the animals treated with apotransferrin in comparison with the controls. The lighter areas in the images (A) of FIGS. 1 and 2 indicate the brain area affected. In both cases, the results clearly demonstrate that the administration of apotransferrin is highly beneficial in reducing the damages caused by transient focal ischemic brain stroke.

Figure 3:
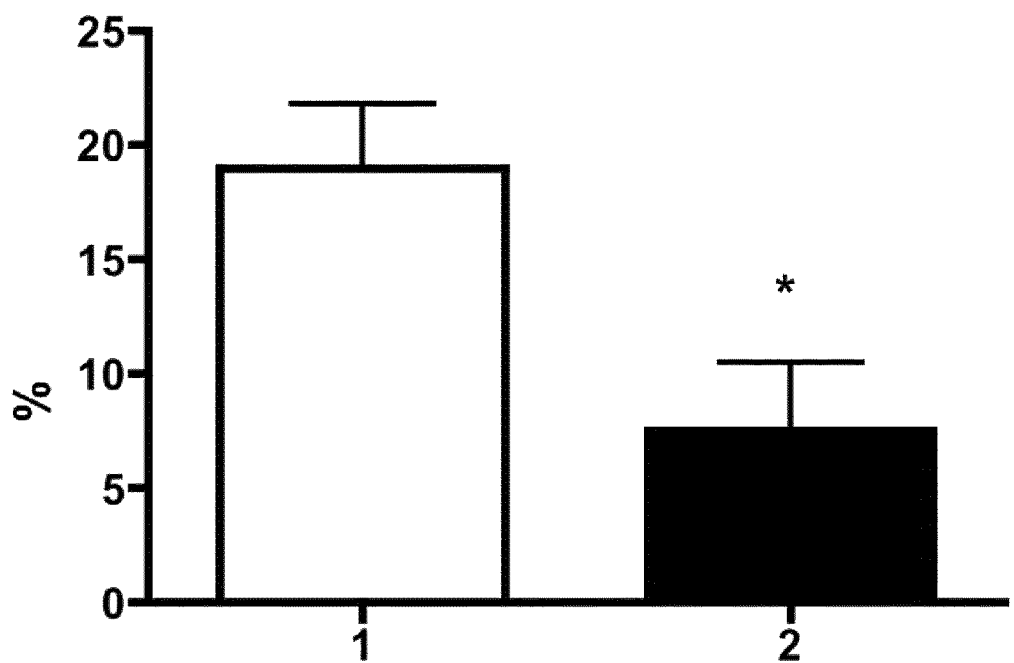
FIG. 3. Percentage of volume of cortical infarction induced in rats by the permanent occlusion of the middle cerebral artery by ligation with administration of: (2) apotransferrin or (1) carrier. With respect to the examples.

The effect of the administration of apotransferrin by intravenous route was also observed in a permanent focal stroke model. FIG. 3 shows how the IV administration of apotransferrin 50 min after the permanent occlusion of the middle cerebral artery was produced in the rats led to a considerable reduction (around 50%) in the volume of damaged brain area. Therefore, the administration of apotransferrin is also effective for the treatment of permanent focal stroke, where the reperfusion of the ischemic tissue does not occur. The animals subjected to permanent occlusion of the middle cerebral artery were also the object of neurological tests with the purpose of assessing their degree of sensorial and motor affectation. The preliminary results of these tests indicated that the rats showed less neurological deficit and performed motor tasks involving the affected brain area with greater efficacy when treated with apotransferrin, thus confirming the previous results.

2. Holo-Transferrin Increases Neuronal Damage in In Vitro and In Vivo Brain Stroke Models.

Figure 4:
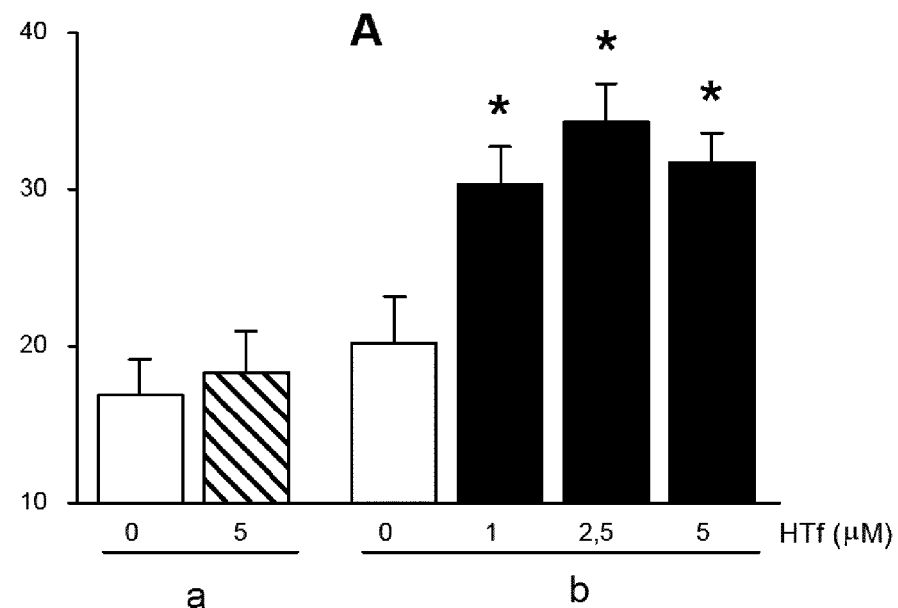
FIG. 4. A, Determination of the effect of different concentrations of holo-transferrin (HTf) over neuronal death in: (a) normoxic cultures or (b) cultures subjected to oxygen-glucose deprivation (OGD) and 30 min of reperfusion. The Y-axis shows the neuronal death determined by the incorporation of propidium iodide in the cells. B, production of free radicals in: (a) neurons in culture control, (1) neurons with addition of 50 µM $FeCl_3$ or (2) neurons with addition of 5 µM HTf. The Y-axis shows the percentage of DCF fluorescence vs OGD/carrier. With respect to the examples.
Figure 4:
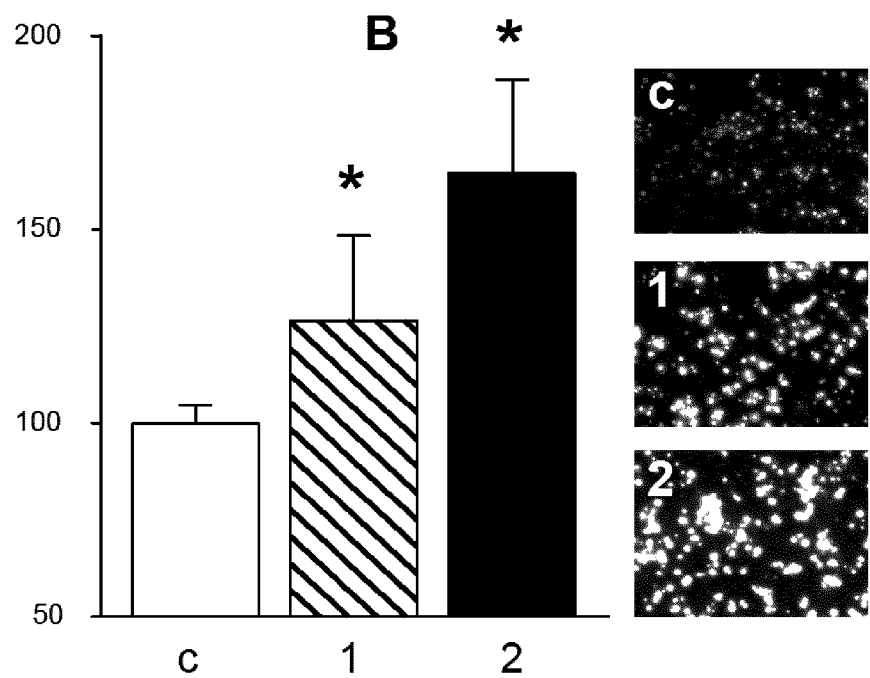
Figure 5:
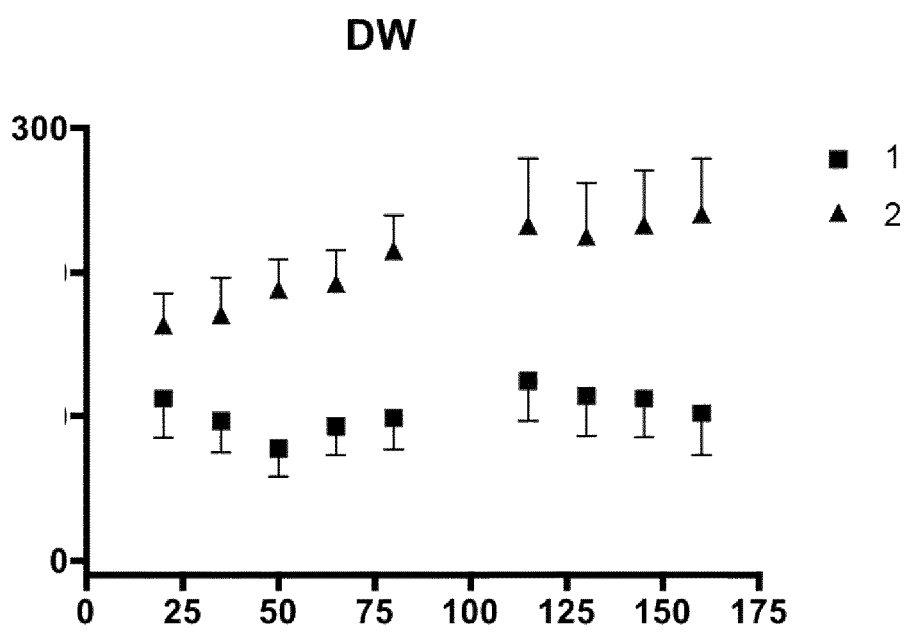
FIG. 5. Neuronal damage measured by nuclear magnetic resonance in rats subjected to the transient occlusion of the middle cerebral artery by intraluminal filament after intravascular injection of carrier (1) or holotransferrin (2). The X-axis represents the time in min whilst the Y-axis represents the volume of neuronal damage in $mm^3$ according to the DWI sequence. With respect to the examples.

The effect of holotransferrin (fraction of transferrin which is saturated with iron) was also studied in an in vitro model of ischemia called OGD. As shown in FIG. 4, holotransferrin induces neuronal death (A) and an extensive production of free radicals (B) in cultured neurons subjected to OGD. It was consistently observed that holotransferrin injected intravascularly before the brain stroke takes place increases the neuronal damage caused by the stroke. FIG. 5 shows the DWI (volume of diffusion-weighted image) measured by nuclear magnetic resonance in animals subjected to a transient focal cerebral ischemia using intraluminal filament. This DWI corresponds to the area of tissue that is going to die. The figure shows that the animals treated with holotransferrin at different times before performing the occlusion of the MCA showed greater DWI than the controls, i.e. they showed greater neuronal damages than the controls.

These results indicate that, unlike apotransferrin, holotransferrin is harmful for brain stroke patients.

The invention claimed is:

1. A method of treatment of acute, focal brain ischemic stroke, wherein the brain stroke is a transient stroke, comprising administering apotransferrin to an animal in need thereof; the administering being by vascular route at one or more of:
   a time selected from about two hours before to about two hours after a reperfusion of said animal, or
   at about the time of a reperfusion of said animal.

2. The method according to claim 1, wherein the administering is at about the time of a reperfusion of said animal.

3. The method according to claim 1, wherein the administering of apotransferrin is by an intravenous or intraarterial route.

4. The method according to claim 1, wherein the administering is at a time selected from about two hours before to about two hours after a reperfusion of said animal.

5. The method according to claim 1, wherein the administering of apotransferrin is in combination with an agent selected from the group consisting of a thrombolytic agent, a chelating agent, citicoline, fluoxetine and lactoferrin.

6. The method according to claim 5, wherein the combination is with a thrombolytic agent.

7. The method according to claim 6, wherein the thrombolytic agent is a human tissue plasminogen activator.

8. The method according to claim 5, wherein the chelating agent is deferoxamine.

9. The method according to claim 1, wherein the dose to be administered of apotransferrin is comprised between 1 and 1000 mg per kg of weight.

10. The method according to claim 1, wherein reperfusion is achieved by surgical intervention to eliminate the clot obstructing the blood flow.

* * * * *